United States Patent
Falck et al.

(10) Patent No.: US 10,114,927 B2
(45) Date of Patent: Oct. 30, 2018

(54) APPARATUS AND METHOD FOR ACOUSTIC ALARM DETECTION AND VALIDATION

(71) Applicant: KONINKLIJKE PHILIPS N.V., Eindhoven (NL)

(72) Inventors: Thomas Falck, Eindhoven (NL); Mun Hum Park, Eindhoven (NL); Armin Gerhard Kohlrausch, Eindhoven (NL); Cornelus Hendricus Bertus Arnoldus Van Dinther, Mierlo (NL)

(73) Assignee: Koninklijke Philips N.V., Eindhoven (NL)

( * ) Notice: Subject to any disclaimer, the term of this patent is extended or adjusted under 35 U.S.C. 154(b) by 240 days.

(21) Appl. No.: 15/033,882

(22) PCT Filed: Oct. 21, 2014

(86) PCT No.: PCT/EP2014/072472
§ 371 (c)(1),
(2) Date: May 2, 2016

(87) PCT Pub. No.: WO2015/062896
PCT Pub. Date: May 7, 2015

(65) Prior Publication Data
US 2016/0283681 A1     Sep. 29, 2016

(30) Foreign Application Priority Data
Nov. 1, 2013   (EP) .................................. 13191274

(51) Int. Cl.
| | | |
|---|---|---|
| *H04R 29/00* | (2006.01) | |
| *G06F 19/00* | (2018.01) | |
| *G16H 40/63* | (2018.01) | |
| *G08B 29/12* | (2006.01) | |
| *G08B 29/24* | (2006.01) | |
| *A61B 5/00* | (2006.01) | |

(52) U.S. Cl.
CPC ......... *G06F 19/3406* (2013.01); *G16H 40/63* (2018.01); *A61B 5/7405* (2013.01); *A61B 2560/0276* (2013.01); *G08B 29/126* (2013.01); *G08B 29/24* (2013.01)

(58) Field of Classification Search
CPC ...................................................... H04R 29/00
See application file for complete search history.

(56) References Cited

U.S. PATENT DOCUMENTS

| | | | |
|---|---|---|---|
| 5,652,566 A | 7/1997 | Lambert | |
| 5,736,927 A * | 4/1998 | Stebbins | G08B 25/085 340/3.32 |
| 6,094,134 A * | 7/2000 | Cohen | G08B 25/14 340/506 |
| 7,106,193 B2 * | 9/2006 | Kovach | G08B 25/00 340/426.1 |
| 7,679,504 B2 | 3/2010 | Wang et al. | |

(Continued)

FOREIGN PATENT DOCUMENTS

WO     2013057652 A2    4/2013

*Primary Examiner* — Olisa Anwah

(57) ABSTRACT

The invention relates to an apparatus and method for use in detecting and validating acoustic alarms, and in particular relates to an apparatus and method for use in detecting and validating acoustic alarms generated by medical devices, such as patient monitoring devices.

20 Claims, 5 Drawing Sheets

(56) References Cited

U.S. PATENT DOCUMENTS

| | | | |
|---|---|---|---|
| 7,962,188 B2 | 6/2011 | Kiani et al. | |
| 9,191,762 B1* | 11/2015 | Matesa | H04R 29/00 |
| 2007/0109115 A1* | 5/2007 | Kiani | A61B 5/1455 |
| | | | 340/507 |
| 2008/0139898 A1 | 6/2008 | Johnson et al. | |
| 2008/0219458 A1* | 9/2008 | Brooks | H03G 3/32 |
| | | | 381/57 |
| 2009/0033505 A1* | 2/2009 | Jones | G08B 25/009 |
| | | | 340/584 |
| 2009/0295591 A1* | 12/2009 | Bedingfield | A61M 1/14 |
| | | | 340/660 |
| 2010/0109869 A1* | 5/2010 | Marr | G08B 13/1654 |
| | | | 340/566 |
| 2010/0315224 A1 | 12/2010 | Orsini et al. | |
| 2011/0054264 A1 | 3/2011 | Fischell et al. | |
| 2011/0087079 A1 | 4/2011 | Aarts | |
| 2012/0029301 A1 | 2/2012 | Battista, Jr. | |
| 2012/0286946 A1 | 11/2012 | Karl et al. | |
| 2013/0077797 A1* | 3/2013 | Hoy | G08B 3/10 |
| | | | 381/56 |
| 2014/0278388 A1* | 9/2014 | Watson | G10L 25/63 |
| | | | 704/231 |
| 2016/0135758 A1* | 5/2016 | Sabota | A61G 11/00 |
| | | | 340/573.1 |

* cited by examiner

APPARATUS AND METHOD FOR ACOUSTIC ALARM DETECTION AND VALIDATION

CROSS-REFERENCE TO PRIOR APPLICATIONS

This application is the U.S. National Phase application under 35 U.S.C. § 371 of International Application No. PCT/EP2014/072472, filed on Oct. 21, 2014, which claims the benefit of U.S. European Patent Application No. 13191274.3, filed on Nov. 1, 2013. These applications are hereby incorporated by reference herein, for all purposes.

TECHNICAL FIELD OF THE INVENTION

The invention relates to an apparatus and method for use in detecting and validating acoustic alarms, and in particular relates to an apparatus and method for use in detecting and validating acoustic alarms generated by medical devices, such as patient monitoring devices.

BACKGROUND TO THE INVENTION

Many medical devices (such as patient monitors, infusion pumps, ventilators, etc.) are configured to generate acoustic alarms. These alarms are usually generated in response to a detected change in the status of the patient or the operation of the device, which may indicate that the patient or device needs urgent attention. Failure to react to an alarm in a timely fashion can therefore jeopardize patient safety.

However; in recent years it has been recognized that when medical devices generate too many acoustic alarms, particularly when many of those alarms indicate non-serious events, medical staff become overwhelmed and "alarm fatigue" occurs. The constant beeping of alarms on patient monitors and other medical devices desensitizes caregivers, causing them to ignore or even disable the sounds that signal that patients may be in danger. Furthermore, the alarm sounds make a lot of noise that is scaring for patients and interrupts their sleep.

Hospitals are therefore being urged to address this serious patient safety issue. One way to mitigate the problem is to reduce or eliminate the generation of acoustic alarms which do not signal a need for urgent action. Ideally, all remaining acoustic alarms will then be medically significant, so it is of the utmost important that these alarms are successful in attracting the attention of medical staff. This can be difficult to ensure in an environment where alarm fatigue has already set in.

Another way to mitigate the problem of excessive alarm sounds in wards is to connect bedside medical devices to remote speakers located outside the ward, but within earshot of medical personnel (for example near a nurses station). The bedside medical devices can then be set to emit alarm sounds through the remote speakers rather than through their own integrated speakers. However, the reliance on a connection to a remote speaker increases the risk of the alarm not being generated properly. This could occur, for example because of a malfunction or incorrect adjustment of the remote speaker, or a failure of the communications link between the bedside medical device and the remote speaker. Furthermore, if several medical devices are connected to the same, or adjacent, remote speakers, concurrent alarms from these devices may lead to one or more of the alarms being drowned out. A similar problem may occur if an alarm is generated during a period when the level of background noise is unusually high.

There is therefore a need for a system which can verify that an acoustic alarm generated by a medical device has been rendered in a sufficiently audible manner.

SUMMARY OF THE INVENTION

According to a first aspect of the invention, there is provided an alarm detection and validation device for validating acoustic alarms that have been generated by a medical device. The alarm detection and validation device comprises a microphone arranged to output a first signal corresponding to audio detected by the microphone. The alarm detection and validation device also comprises an alarm sound database containing audio signals corresponding to known alarm sounds, including the acoustic alarms able to be generated by the medical device. The alarm detection and validation device also comprises a processing unit arranged to receive the first signal from the microphone; receive a second signal from the medical device indicating that the medical device has generated an acoustic alarm; analyze the first signal to determine whether the detected audio includes the acoustic alarm generated by the medical device by comparing the detected audio to the audio signals in the alarm sound database so as to identify known alarm sounds included in the detected audio; and output a third signal to the medical device based on the result of the determination, if the result of the determination is that the detected audio includes the acoustic alarm generated by the medical device.

In particular embodiments of the invention the processing unit is can be arranged to output the third signal if the result of the determination is that the detected audio does not include the acoustic alarm generated by the medical device.

In particular embodiments of the invention, the third signal can comprise a notification of the result of the determining.

In particular embodiments of the invention the third signal can comprise an instruction to the medical device to (a) alter one or more parameters of the acoustic alarm, wherein the one or more parameters include any or all of: alarm volume, alarm pattern, alarm spectral composition, which loudspeaker is used to emit the alarm; and/or (b) generate a non-acoustic alarm.

In a specific embodiment the processing unit can be further arranged to determine a current sound pressure level; and use the determined sound pressure level to compare the volume of an acoustic alarm identified in the detected audio with the volume of other sounds included in the detected audio.

In the specific embodiment the processing unit can be further arranged to determine one or more parameters associated with an acoustic alarm included in the detected audio which has been identified by the sound classifier as being generated by the medical device; determine one or more parameters associated with a different acoustic alarm included in the detected audio which has been identified by the sound classifier as being generated by a device other than the medical device; and compare the one or more parameters of the acoustic alarm with the one or more parameters of the different acoustic alarm.

In the specific embodiment the third signal can comprise an instruction to the medical device to alter one or more parameters of the acoustic alarm to be different to the one or more parameters of the different acoustic alarm. The one or more parameters can include any or all of: alarm volume, alarm pattern, alarm spectral composition. Altering the one or more parameters of the acoustic alarm to be different to the one or more parameters of the different acoustic alarm may enable the acoustic alarm generated by the medical device to be more easily distinguished from the different acoustic alarm.

According to a second aspect of the invention, there is provided a medical device comprising a loudspeaker for emitting an acoustic alarm generated by the medical device; an alarm detection and validation device according to the first aspect of the invention, wherein the microphone of the alarm detection and validation device is arranged such that the detected audio includes any acoustic alarms emitted by the loudspeaker; and a processing unit. The processing unit is arranged to cause the loudspeaker to emit an acoustic alarm; send a signal to the alarm detection and validation device indicating that the medical device has generated an acoustic alarm; and perform a further action in response to (a) receiving the third signal output by the alarm detection and validation device, wherein the further action is based on the third signal; or (b) not receiving a signal from the alarm detection and validation device within a predetermined time period.

In particular embodiments the further action can comprise one or more of: cause the loudspeaker to continue emitting the acoustic alarm in accordance with the current parameters; alter one or more of the predefined parameters and cause the loudspeaker to emit the acoustic alarm in accordance with the altered parameters; cause the loudspeaker to cease emitting the acoustic alarm; cause a different loudspeaker to emit the acoustic alarm; cause an alternative alarm means to emit a non-acoustic alarm.

In particular embodiments the medical device can comprises a main body which houses at least the processing unit of the medical device; one or more remote components able to be positioned remotely from the main body, which house at least the loudspeaker and the microphone; and a communications interface for enabling communication between the processing unit in the main body and the one or more remote components.

In particular embodiments the medical device can further comprise alternative alarm means for generating a non-acoustic alarm. In such embodiments the processing unit of the medical device can be further arranged to cause the alternative alarm means to generate a non-acoustic alarm. In such embodiments the processing unit of the medical device can be arranged to cause the alternative alarm means to generate a non-acoustic alarm (a) if the medical device has not received a signal from the alarm detection and validation device within the predetermined time period; or (b) wherein the processing unit of the alarm detection and validation device is also arranged to output the third signal if the result of the determination is that the detected audio does not include the acoustic alarm generated by the medical device, if the third signal is based on the alarm detection and validation device having determined that the detected audio does not include the acoustic alarm generated by the medical device.

In particular embodiments the medical device can further comprise an additional loudspeaker located within or adjacent to the main body of the medical device. In such embodiments the processing unit of the medical device can be arranged to cause the additional loudspeaker to emit an acoustic alarm: (a) if the third signal is based on the alarm detection and validation device having determined that the detected audio does not include the acoustic alarm generated by the medical device; or (b) wherein the processing unit of the alarm detection and validation device is also arranged to output the third signal if the result of the determination is that the detected audio does not include the acoustic alarm generated by the medical device, if the third signal is based on the alarm detection and validation device having determined that the detected audio does not include the acoustic alarm generated by the medical device.

According to a third aspect of the invention, there is provided a method for validating an acoustic alarm generated by a medical device. The method comprises: (a) providing a microphone arranged such that sound emitted by a loudspeaker configured to emit acoustic alarms generated by the medical device will be included in audio detected by the microphone; (b) providing an alarm sound database containing audio signals corresponding to known alarm sounds, including the acoustic alarms able to be generated by the medical device; (c) providing a processing unit in communication with both the medical device and the microphone; (d) generating an acoustic alarm with the medical device; (e) notifying the processing unit of the generation of the acoustic alarm; (f) detecting audio with the microphone; (g) analyzing, with the processing unit, the detected audio to determine whether it includes the acoustic alarm generated by the medical device by comparing the detected audio to the audio signals in the alarm sound database so as to identify known alarm sounds included in the detected audio; and if it is determined in (g) that the detected audio includes the acoustic alarm generated by the medical device: (h) outputting, with the processing unit, a signal to the medical device based on the result of the determining.

In a specific embodiment, the method further comprises performing (h) if it is determined in (g) that the detected audio does not include the acoustic alarm generated by the medical device.

In the specific embodiment, the method can further comprise receiving, at the medical device, the signal output by the processing unit; and performing, by the medical device, a further action. In the specific embodiment the further action can be performed in response to (a) receiving the signal output by the processing unit, wherein the further action is based on the signal output by the processing unit; (b) not receiving a signal from the processing unit within a predetermined time period. In the specific embodiment the further action can comprise one or more of: cause the loudspeaker to continue emitting the acoustic alarm in accordance with the current parameters; alter one or more of the predefined parameters and cause the loudspeaker to emit the acoustic alarm in accordance with the altered parameters; cause the loudspeaker to cease emitting the acoustic alarm; cause a different loudspeaker to emit the acoustic alarm; cause an alternative alarm means to emit a non-acoustic alarm.

In the specific embodiment, the step of analyzing can comprise comparing the detected audio to audio signals corresponding to known alarm sounds.

In the specific embodiment, the step of analyzing can comprise (i) comparing the volume of an acoustic alarm included in the detected audio with the volume of background noise included in the detected audio. In the specific embodiment the step of analyzing can, additionally or alternatively to (i), comprise (ii) comparing one or more parameters of an acoustic alarm included in the detected audio with one or more parameters of a different acoustic alarm included in the detected alarm signal. In the specific embodiment the method can further comprises altering one or more parameters of the acoustic alarm generated by the medical device based on the result of (i) and/or (ii).

According to a fourth aspect of the invention, there is provided a computer program product comprising computer readable code embodied therein, the computer readable code being configured such that, on execution by a suitable computer or processing unit, the computer or processing unit performs method steps (f) and (g) according to the third aspect of the invention.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
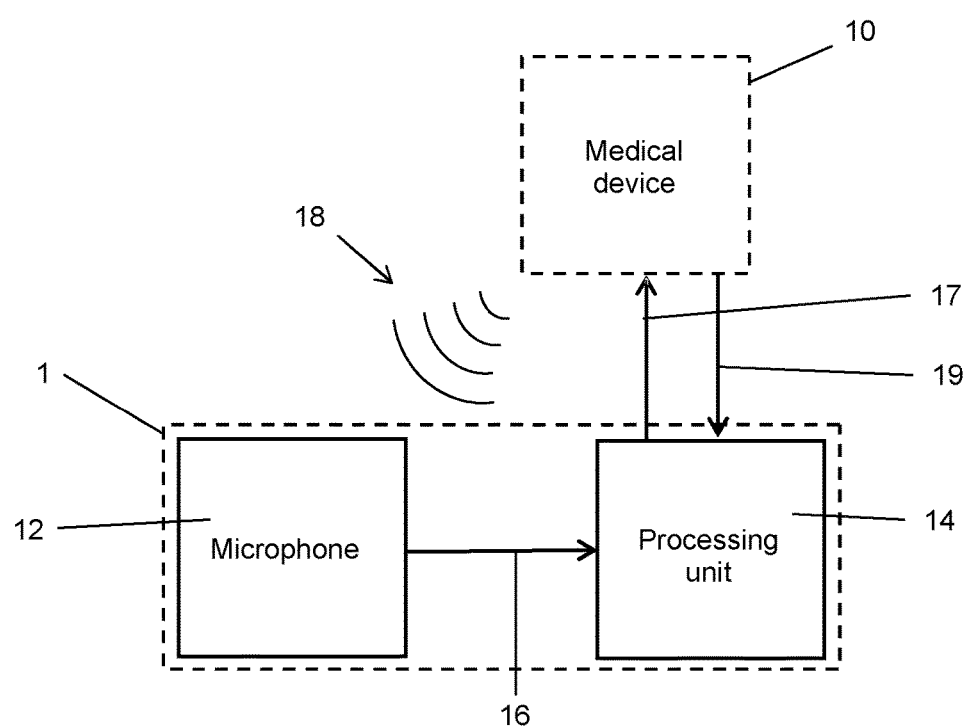
FIG. 1 is an illustration of an alarm detection and validation device according to a general embodiment of the invention.

FIG. 1 shows an alarm detection and validation device (hereafter referred to as a "validation device") 1 according to an embodiment of the invention. The validation device 1 shown in FIG. 1 is for detecting and validating acoustic alarms that have been generated by a medical device 10 (such as, for example, a patient monitor, a ventilator or an infusion pump). The outlines of the medical device 10 and the validation device 1 are depicted in FIG. 1 using dashed lines to indicate that these devices need not be provided as separate components.

The validation device 1 comprises a microphone 12 that is arranged to output a first signal 16 corresponding to audio 18 detected by the microphone. In some embodiments the microphone is non-directional and therefore able to detect all sounds produced within its range. In other embodiments a directional microphone is used, arranged so that only sounds originating from the direction of a particular sound emitting device are detected. Preferably the range of the microphone, whether directional or non-directional, is limited to be not significantly greater than the distance between the microphone and a loudspeaker used to emit the acoustic alarm being validated. For example, the range of the microphone may be limited to approximately 5 meters.

The validation device 1 further comprises a processing unit 14 which is arranged to receive the first signal 16 from the microphone 12. The processing unit 14 is also arranged to receive a second signal 19 from a medical device 10. The second signal 19 indicates that the medical device 10 has generated an acoustic alarm. The processing unit 14 is further arranged to analyze the first signal 16 to determine whether the audio 18 detected by the microphone 12 includes the acoustic alarm generated by the medical device 10, and to output a third signal 17 to the medical device 10 based on the result of this determination.

Thus the validation device 1 receives both a signal from the medical device 10 indicating that it has generated an acoustic alarm, and a signal from the microphone 12 from which the validation device can determine whether the microphone has detected an acoustic alarm. This enables the device 1 to be used to validate alarms generated by the medical device 10 (i.e. to check that such alarms have actually been emitted, and in a sufficiently audible manner). In some embodiments the validation device also includes a memory (not shown), which can be used to store the signals received from the microphone and/or the results of the analysis performed on those signals.

Figure 2A:
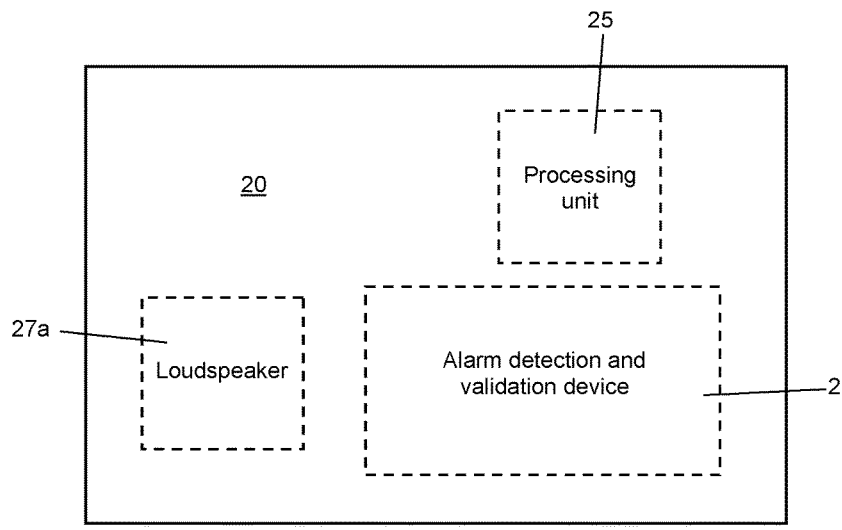
FIG. 2a is an illustration of a medical device according to a first specific embodiment of the invention.

In some embodiments the validation device 1 is an integral part of the medical device 10. FIG. 2a illustrates an example of such an embodiment. The medical device 20 shown in FIG. 2a includes a sound emitting device (in this case a loudspeaker) 27a for emitting acoustic alarms generated by the medical device 20. The loudspeaker 27a and the microphone (not shown) are both integral with the main housing of the medical device 20. The microphone is located appropriately in relation to the loudspeaker 27a such that the microphone is able to detect sounds emitted by the loudspeaker 27a. For example, if a directional microphone is used, it should be directed toward the loudspeaker 27a. Preferably, the arrangement of the microphone is such that it is also able to detect other sounds (i.e. sounds which are not emitted by the loudspeaker 27a), such as acoustic alarms emitted by other medical devices and general background noise. The processing unit 24 of the validation device 2 is directly connected to a processing unit 25 of the medical device 20. It will be appreciated, however, that in some embodiments the processing unit 24 of the validation device can be the same as the processing unit 25 of the medical device 20.

Figure 2B:
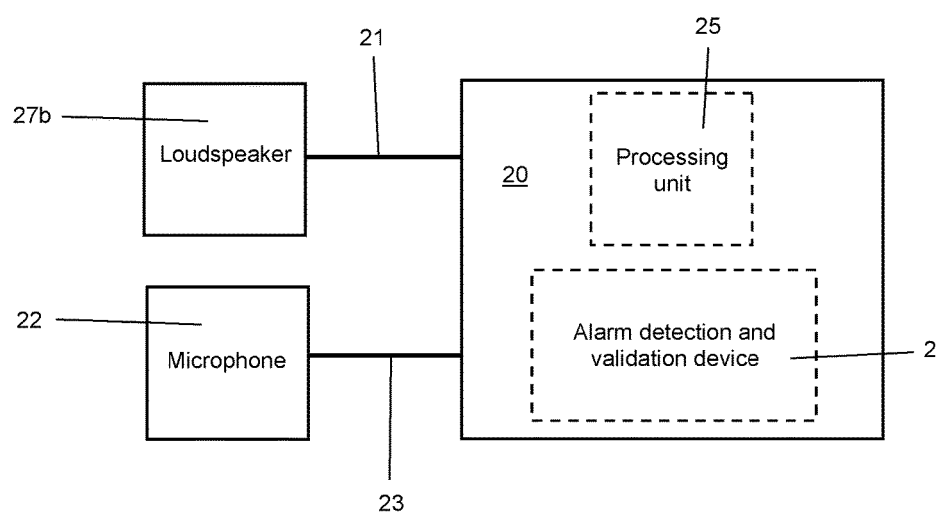
FIG. 2b is an illustration of a medical device according to a second specific embodiment of the invention.

In alternative embodiments, such as that illustrated in FIG. 2b, a sound emitting device (in this case a loudspeaker) 27b is provided as a separate component. The loudspeaker 27b is connected to the main housing of the medical device 20 by a cable 21 (although it will be appreciated that a wireless connection could be used instead). The loudspeaker 27b receives power and control signals from the medical device 20 by means of this cable 21. Likewise, a microphone 22 is also provided as a separate component, connected to the main housing of the medical device 20 by a cable 23 (although it will be appreciated that a wireless connection could be used instead). The microphone 22 uses the cable 23 to receive power and control signals from the medical device 20 and to sends signals corresponding to detected audio to the medical device 20. Preferably the cable 23 is long enough to allow the microphone 22 to be located at an appropriate position in relation to the loudspeaker, as described above. Embodiments of the invention in which the sound emitting device and microphone are separate from the main body of the medical device are advantageous because they permit greater flexibility in the positioning of the sound emitting device. For example, the sound emitting device can be positioned facing away from the patient's bed, so that acoustic alarms are better projected into the room for improved audibility by medical staff and are less disturbing for the patient. Additionally, such embodiments allow the medical device to be placed in close proximity to other medical devices without affecting the efficacy of the sound emitting device.

In other embodiments (not specifically illustrated) the validation device 1 is separate from the medical device 10. In such embodiments the validation device 1 is a stand-alone device having its own power supply (for example in the form of a battery, and/or a lead for connecting the validation device to an external power supply or mains electricity) and its own processing unit. In these embodiments the validation device 1 further includes a communications interface for communicating with the medical device 10. The communications interface may be a wireless communications interface, which enables communication by means of a wireless communication protocol such as Wi-Fi, Bluetooth, ZigBee, or a cellular telecommunications network, etc. In some embodiments the validation device 1 includes a wireless communications interface and its power supply comprises a battery. These features enhance the portability of the validation device 1, allowing it to be used in almost any location within range of the wireless communications technology being employed. Alternative embodiments of the validation device 1 include a wired communications interface. In some embodiments, communication between the validation device 1 and the medical device 10 is effected via a hospital network to which both devices are connected. Connection of the validation device 1 to the hospital network may be wired or wireless. Providing the validation device 1 as a standalone device advantageously allows it to be used to validate the generation of acoustic alarms in a silent ICU arrangement, in which medical devices are configured to send acoustic alarms to a remote speaker located outside of the room in which the medical devices are located. This scenario is described in more detail below, with reference to FIG. 5.

In use, the validation device 1 is positioned such that audio detected by the microphone will include sound emitted by the sound emitting device (hereinafter referred to a loudspeaker, although it will be appreciated that other types of sound emitting devices could be used) used by the medical device 1 to generate acoustic alarms. If the medical device 10 is configured to use an integral loudspeaker, the microphone 12 should be positioned near to the medical device. If, on the other hand, the medical device 10 is arranged to use a loudspeaker which is located away from the main housing of the medical device, the microphone 12 should be positioned near to the loudspeaker. If the validation device 1 is provided as an integral part of the medical device 10 then the relative positions of the microphone and loudspeaker will have been considered during manufacture of the medical device 10, as described above.

Communications links are established between the processing unit 14 of the validation device and the microphone 12, and between the processing unit 14 and the medical device 10. Establishing these communications links may include any or all of: switching on the validation device; enabling a validation mode on the medical device and/or on the validation device; connecting a cable between the medical device and or the validation device; connecting the medical device and/or the validation device to a hospital network; setting up a wireless connection between the validation device and the medical device.

In embodiments of the invention where the validation device 1 is a stand-alone device, the processing unit 14 is directly connected to the microphone 12 by means of, for example, an electrical circuit. In some such embodiments a switch is provided in the circuit to enable/disable the connection between the microphone 12 and the processing unit 14. In these embodiments, establishing the communications link between the processing unit 14 and the microphone 12 includes setting the switch such that the connection is enabled, for example by activating a "validation mode" of the validation device 1. Furthermore, a wired or wireless communications link between the stand-alone validation device 1 and the medical device 10 must be established according to the type of communications interfaces present in the validation device 1 and the medical device 10.

In embodiments of the invention where the validation device 2 is integral with the medical device 20 (as shown in FIGS. 2a and 2b), communication between the processing unit and the medical device 20 comprises communication between the processing unit of the validation device 2 and a processing unit 25 of the medical device 20. Alternatively, if the processing unit of the validation device is the same as the processing unit of the medical device, communication between the processing unit and the medical device 20 comprises communication between different parts of the processing unit. In both cases the communication is directly effected by means of signals passed through electrical circuits.

In embodiments of the invention where both the validation device 2 and the microphone are integral with the medical device 20 (as shown in FIG. 2a), the microphone is directly connected by an electrical circuit to either the processing unit of the validation device 2 or to a processing unit 25 of the medical device 20 (which is itself directly connected to the processing unit of the validation device 2). In some such embodiments a switch is provided in the circuit to enable/disable the connection between the microphone and the processing unit. In these embodiments establishing a communications link between the processing unit and the microphone comprises setting the switch such that the connection is enabled, for example by activating a "validation mode" of the medical device 20. In alternative embodiments where the microphone 22 is not integral with the main body of the medical device 20 (as shown in FIG. 2b), establishing a communications link between the processing unit and the microphone 22 comprises connecting the microphone 22 to the medical device 20 (and thereby to the processing unit of the validation device) by any suitable means, according to the communications interfaces present in the microphone 22 and the medical device 20.

Figure 3:
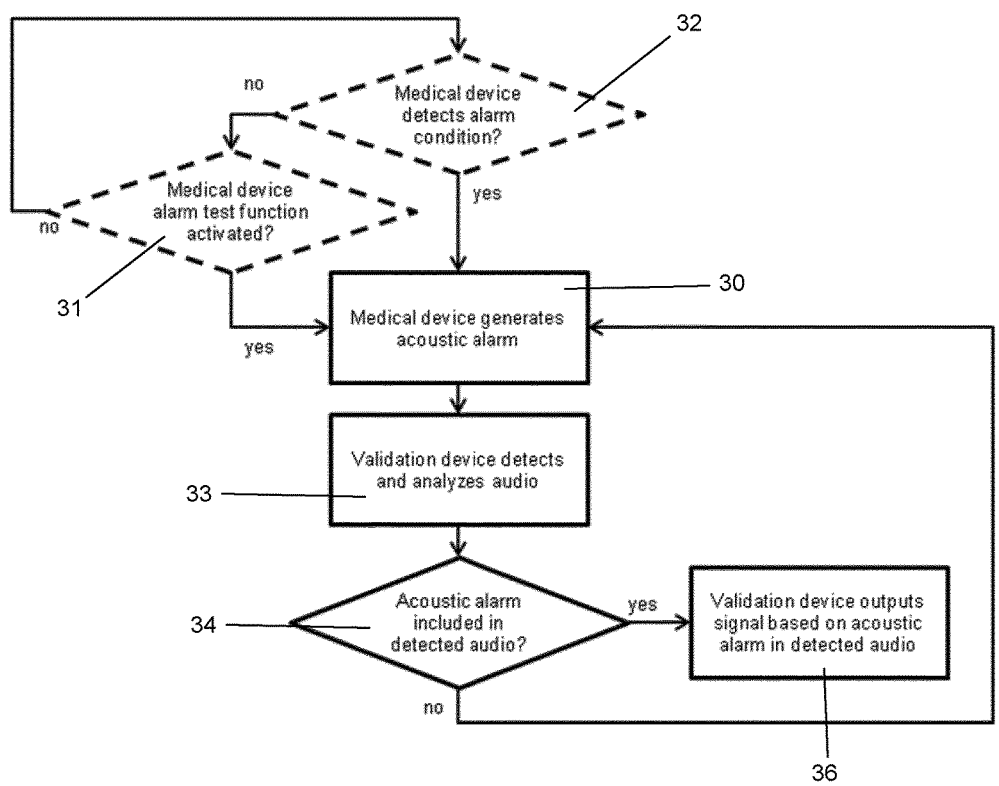
FIG. 3 is a flow chart illustrating a method for detecting and validating acoustic alarms generated by a medical device according to a general embodiment of the invention.

When the validation device 1 and the medical device 10 have been set up as described above, an alarm detection and validation method is carried out. This method is illustrated in FIG. 3. In a first step 30 the medical device 10 generates an acoustic alarm. The reason for the acoustic alarm being generated is not relevant to the performance of the validation method and is therefore outside the scope of the present invention. However, the generation of the acoustic alarm could be as a result of a member of the medical personnel manually activating a "test" function of the medical device 10, as shown by block 31. Alternatively, the acoustic alarm may be generated as part of the normal functioning of the medical device 10, for example as a result of the medical device 10 detecting an alarm condition (block 32). (Blocks 32 and 31 are depicted using dashed lines to indicate that these actions do not form part of the alarm detection and validation method.)

Generation 30 of the acoustic alarm comprises a processing unit of the medical device 10 sending a signal to a loudspeaker to cause it to emit sound. Generation 30 of the acoustic alarm also involves the medical device 10 sending a signal 19 to the processing unit 14 of the validation device 1 indicating that an acoustic alarm has been generated. In some embodiments the signal 19 is the same as the signal sent to the loudspeaker. In these embodiments the processing unit 14 is configured to interpret the signal 19 as a notification that an acoustic alarm has been generated. The signal 19 may be sent concurrently with the signal from the medical device 10 to the loudspeaker. Alternatively, the signal 19 to the processing unit 14 may be sent before or after the signal to the loudspeaker. Preferably the signal 19 indicates the time at which the acoustic alarm was generated (i.e. the time at which the processing unit of the medical device signalled or expects to signal the loudspeaker to emit the acoustic alarm). Preferably the signal 19 also indicates the type of acoustic alarm generated.

In a second step 33 of the validation method the validation device 1 detects audio (with the microphone 12) and analyzes the detected audio (with the processing unit 14). In some embodiments the microphone 12 is activated when the medical device 10 generates an acoustic alarm. For example, in embodiments where the signal 19 is sent before or concurrently with the signal to the loudspeaker, the processing unit 14 can activate the microphone in response to receiving the signal 19. Alternatively, the microphone 12 can be activated in response to the medical device 10 and/or the validation device 1 being put into a "validation mode". Such embodiments have the advantage of saving power and processing resources, since only audio signals which are likely to include acoustic alarms are detected and analyzed. In alternative embodiments the microphone 12 may be manually activated by a member of the medical personnel. In still other embodiments the microphone 12 is constantly activated.

Once activated, the microphone 12 detects all sounds within its range. Depending on factors such as the location of the microphone 12 and the time of day, the detected audio is likely to include background sounds such as vocalizations of the patient, other patients and/or medical staff; non-vocal patient noises (i.e. coughs, sneezes, movement noises etc.); sounds caused by movement of furniture; footsteps; acoustic alarms generated by other medical devices; etc. If the acoustic alarm generated by the medical device 10 is successfully emitted by the loudspeaker then the detected audio will include the sound of this acoustic alarm. However; if the generated acoustic alarm is not successfully emitted (e.g. because of a failure of the communications link or the power supply of the loudspeaker; or a volume setting of the acoustic alarm being too low) the detected audio will include only background sounds (if present). The microphone 12 converts the detected audio into an electrical signal 16 (hereafter referred to as the "audio signal") and transmits this signal to the processing unit 14 for analysis.

In some embodiments the processing unit 14 is arranged to deactivate the microphone 12 after a certain amount of time has passed since the generation of the acoustic alarm (in these embodiments the signal 19 will have indicated the time of generation of the acoustic alarm). This time period may be pre-set by a user of the validation device 1. The time period may be defined based on the duration of the alarm sound(s) the medical device 10 is arranged to generate. For example, the time period may be at least as long as the longest alarm sound duration plus the travel time of sound from the loudspeaker to the microphone 12. In other embodiments the detected audio is analyzed in real time by the processing unit 14 and the microphone 12 is deactivated in response to the processing unit 14 determining that the generated acoustic alarm is included in the detected audio.

In some embodiments the processing unit 14 saves the audio signal 16 to a memory of the validation device 1. This enables a record of emitted acoustic alarms to be kept, which can be useful in efforts to address alarm fatigue. Such a record may also be useful if it becomes necessary to prove that a particular acoustic alarm was emitted, for example in a legal dispute. Saving the audio signal to a memory also means that analysis of the audio signal 16 can be performed at a later time, if desired. In some embodiments the analysis is initiated when the microphone 12 is deactivated. Preferably, however, the analysis of the audio signal 16 is performed in real time or near-real time.

In one exemplary embodiment the processing unit 14 includes one or more filters through which the audio signal 16 is passed to detect signatures of particular sound events. The filtered signal is then digitized by a digitizer, which may be an analogue-to-digital converter or the like. A sound classifier then classifies the filtered, digitized signal to identify the type of sound events included in the signal (i.e. an acoustic alarm generated by the medical device 10, 20, an acoustic alarm generated by another medical device, a patient vocalization, etc.). The sound classifier does this by comparing the sound event signatures in the audio signal 16 with a database of sound event signatures corresponding to known types of sound event. The sound classifier may be pre-trained to recognize various sounds commonly encountered in medical environment, including the particular sounds corresponding to acoustic alarms generated by a variety of different medical devices. Preferably the sound classifier is pre-trained to recognize at least the acoustic alarm(s) able to be generated by the medical device 10 which being validated. Preferably each sound event is tagged with a timestamp. In some embodiments the processing unit 14 also includes a sound level analyzer for determining the current sound pressure level.

Information comprised in the signal 19 may also be used in the analysis performed by the processing unit 14. For example, in some embodiments the processing unit 14 compares the timestamp of a sound event identified as an acoustic alarm able to be generated by the medical device 10 with the time of generation of the acoustic alarm indicated in the signal 19. If the timestamp of the sound event is incompatible with the sound event being the generated acoustic alarm (e.g. if the sound event occurs before the acoustic alarm was generated) the processing unit 14 determines that the sound event under consideration is not the acoustic alarm generated by the medical device.

In step 34 the processing unit 14 uses the results of the analysis to determine whether the generated acoustic alarm is included in the detected audio. In some embodiments (e.g. those in which the microphone is deactivated after a certain time period has elapsed) the audio signal 16 analyzed by the processing unit 14 has a finite length corresponding to the period of time the microphone 12 was active for. In these embodiments the processing unit 14 can make a definite determination that the generated acoustic alarm is or is not included in the audio signal 16. Similarly, in some embodiments the processing unit 14 is configured to analyze only a portion of the audio signal 16 corresponding to a predetermined time period starting from the generation of the acoustic alarm. In other embodiments (e.g. those where the microphone is constantly activated) the processing unit 14 continuously receives the audio signal 16. In some such embodiments the processing unit 14 is arranged to determine that the generated alarm is included if, for example, the sound classifier identifies a detected sound event as having the same signature as the type of alarm generated by the medical device (as indicated in the signal 19), but is not arranged to determine that the generated alarm is not included in the detected audio.

In these embodiments (and in other embodiments) the processing unit 14 of the validation device is configured to only send a signal 17 to the medical device 10 if it determines that the acoustic alarm is included in the detected audio. In such embodiments the medical device 10 will be configured to treat the absence of a signal 17 from the validation device as an indication that the acoustic alarm has not been successfully emitted, as is discussed further below in relation to FIG. 4. In alternative embodiments in which the processing unit 14 is arranged to determine that the generated alarm is not included in the detected audio (not shown in FIG. 3), the processing unit 14 outputs a signal 17 to the medical device 10 based on the negative determination. In all embodiments, if the processing unit 14 determines that the audio signal 16 does include the acoustic alarm generated by the medical device 10, in step 36 it outputs a signal 17 to the medical device 10 based on this positive determination. In some embodiments the signal 17 comprises a simple notification that the acoustic alarm was or was not detected in the audio signal 16. In other embodiments the signal 17 comprises an instruction to the medical device 10 to perform a further action (for example to alter the volume or one or more other parameters of the generated acoustic alarm, cause a different loudspeaker to emit the generated acoustic alarm, or generate a non-acoustic alarm).

In some embodiments (not illustrated), if the processing unit 14 determines that the audio signal 16 includes the generated acoustic alarm, it performs further analysis on the audio signal 16 to determine properties of the sound event corresponding to the acoustic alarm, and/or properties of other sound events included in the audio signal 16. In some embodiments this further analysis involves comparing the volume of the acoustic alarm sound event to the volume of other sound events included in the audio signal 16 and/or to the current sound pressure level. It may also involve determining how similar the signature of the acoustic alarm sound event is to the signatures of other sound events included in the audio signal 16. Where the audio signal 16 includes sound events which are identified as acoustic alarms generated by other medical devices, the properties of these acoustic alarms may be determined and compared to the properties of the acoustic alarm generated by the medical device 10. In such embodiments the results of the further analysis may be included in the signal 17 output to the medical device 10. Alternatively or additionally, the processing unit 14 may use the results of the further analysis to generate instructions to the medical device 10 to perform one or more further actions. These instructions are then included in the signal 17 sent to the medical device 10.

Figure 4:
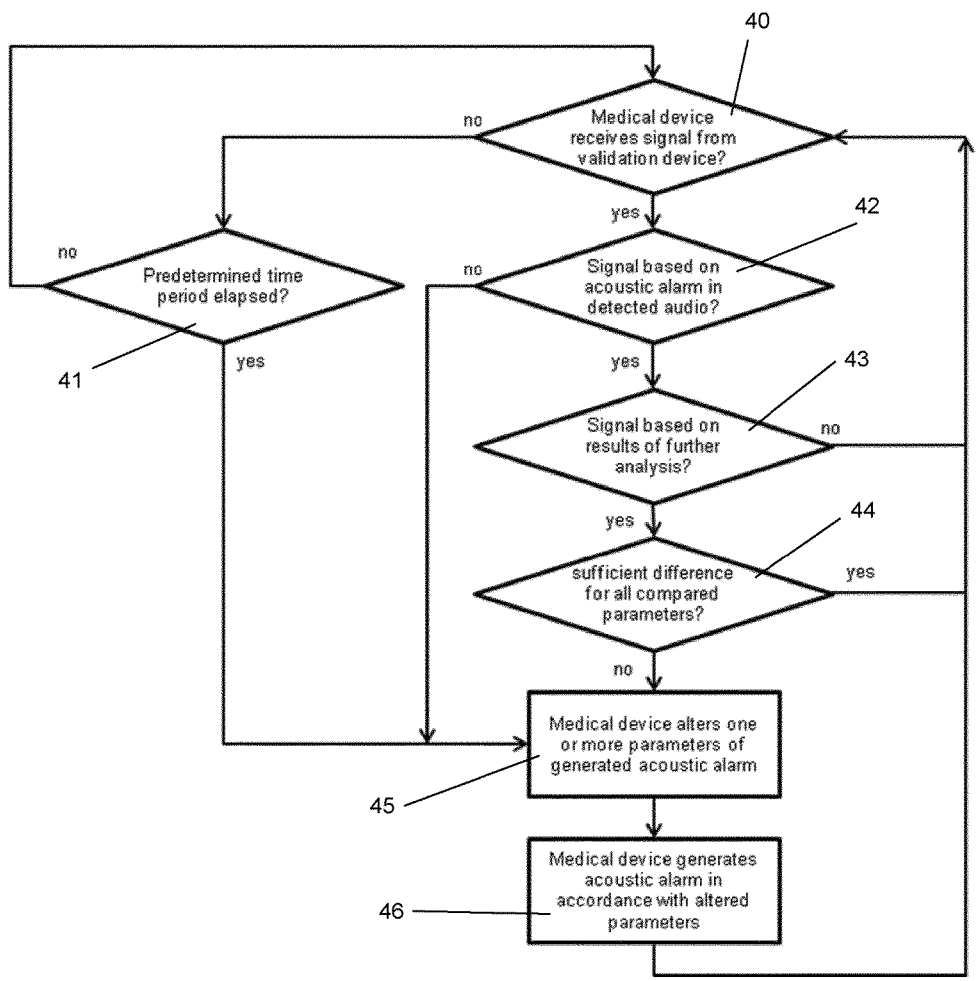
FIG. 4 is a flow chart illustrating a process performed by a medical device being validated according to embodiments of the invention.

FIG. 4 illustrates a process which is implemented by a medical device 10 which has generated an acoustic alarm and which is being validated by a validation device according to embodiments of the invention. In a first step 40 the medical device checks whether it has received a signal 17 from the validation device 1. In the embodiment shown in FIG. 4, if the medical device 10 has not received a signal 17, at step 41 it checks whether a predetermined time period has elapsed since the medical device last generated an acoustic alarm. Preferably the predetermined time period is at least as long as the total of: the duration of the longest alarm sound which the medical device 10 is arranged to generate, the sound travel time between the loudspeaker and the microphone 12, the processing time required to analyze the audio signal 16 (which will, in some embodiments, depend on how long the microphone is arranged to be activated for), and the time required for a signal to be communicated between the processing unit 14 and the medical device 10. In some embodiments the processing time and signal communication time will be programmed into the medical device 10 during its manufacture, based on a measurement of these factors. Preferably the predetermined time period is a few seconds longer than the duration of the longest alarm sound. If the predetermined time period has not elapsed, the medical device 10 continues to periodically check for the receipt of a signal 17. If, on the other hand, the medical device 10 determines at step 41 that the predetermined time period has elapsed, it treats this as an indication that the generated acoustic alarm has not been successfully emitted and the method moves to step 45, described below. It will be appreciated that other embodiments are possible in which the medical device does not perform step 41 and instead repeats step 40 until a signal 17 is received.

If the medical device 10 determines that a signal 17 has been received from the processing unit 14 of the validation device 1, the medical device 10 then, at step 42, determines whether the signal 17 is based on the validation device 1 having determined that the audio signal 16 includes the generated acoustic alarm. If the medical device 10 determines that the signal 17 is based on the validation device 1 having determined that the detected audio does not include the generated acoustic alarm, it treats this as an indication that the generated acoustic alarm has not been successfully emitted and the method moves to step 45, described below.

If, on the other hand, at step 42 the medical device 10 determines that the signal 17 is based on the validation device 1 having determined that the detected audio does include the generated acoustic alarm, the medical device treats this as an indication that the generated acoustic alarm has been successfully emitted. However, in some embodiments the validation device 1 is arranged to perform further analysis on the detected audio, for example to assess how audible and/or effective the acoustic alarm is likely to have been. Therefore, at step 43 the medical device 10 checks whether the signal 17 is based on such further analysis. If the medical device 10 determines that the signal 17 is not based on such further analysis (e.g. it comprises only a notification that the acoustic alarm was determined to be included in the detected audio) it takes no further action (other than continuing to issue the generated acoustic alarm in accordance with the current parameters, if appropriate) and continues to periodically check for signals from the validation device 1.

If the medical device 10 determines that the signal 17 is based on the results of further analysis performed by the validation device, at step 44 it checks whether the signal 17 indicates that the generated acoustic alarm is sufficiently different from other sounds included in the detected audio in respect of all the parameters considered in the further analysis.

In embodiments where the further analysis involves comparing the volume of the acoustic alarm sound event to the volume of other sound events included in the audio signal 16 and/or to the general background volume, the processing unit 14 of the validation device 1 makes a determination as to whether the volume of the acoustic alarm sound event is sufficiently high in relation to the volume of other sound events included in the audio signal 16 and/or to the general background volume (for example as represented by the current sound pressure level determined by a sound level analyzer). This determination may be based, for example, on a pre-defined threshold corresponding to a minimum volume difference between the volume of the acoustic alarm sound event and the volume of other sound events included in the audio signal 16 and/or the general background volume.

In embodiments of the invention where the further analysis involves determining how similar the signature of the acoustic alarm sound event is to the signatures of other sound events included in the audio signal 16, the processing unit 14 makes a determination as to whether the signature of the acoustic alarm sound event is sufficiently different to the signatures of other sound events included in the audio signal

16. Preferably the determination involves determining whether any of the other sound events correspond to acoustic alarms generated by other medical devices. The determination may be based, for example, on a pre-defined threshold corresponding to a minimum value for a measure of difference between sound event signatures. In some embodiments more than one pre-defined threshold may be set. For example, in some embodiments a first pre-defined threshold is used when comparing the signature of the acoustic alarm sound event to the signatures of sound events which correspond to other acoustic alarms and a second, different pre-defined threshold is used when comparing the signature of the acoustic alarm sound event to the signatures of sound events not corresponding to other acoustic alarms. The determination may involve comparing properties of the generated acoustic alarm such as alarm volume, alarm pattern and alarm spectral composition to corresponding properties of other acoustic alarms included in the detected audio signal 16.

The signal 17 may comprise an indication of the result of the determinations (i.e. whether or not the acoustic alarm is sufficiently different from other sounds included in the detected audio in respect of each of the parameters considered during the further analysis), in which case a processing unit of the medical device 10 is preferably configured to determine whether or not to alter one or more parameters of the generated acoustic alarm based on the result. Alternatively, the processing unit 14 of the validation device 1 can be configured to determine whether or not the medical device 10 should alter one or more parameters of the generated acoustic alarm based on the result, in which case signal 17 will include instructions to the medical device 10 to perform such an alteration if the validation device 1 determines that one or more parameters of the generated acoustic alarm should be altered.

If the medical device 10 determines at step 44 that the signal 17 indicates that the generated acoustic alarm is sufficiently different from other sounds included in the detected audio in respect of all of the parameters considered during the further analysis, it treats this as an indication that the generated acoustic alarm has been successfully emitted in a sufficiently audible and/or effective manner. The medical device 10 therefore takes no further action (other than continuing to issue the generated acoustic alarm in accordance with the current parameters, if appropriate) and continues to periodically check for signals from the validation device 1.

If the medical device 10 determines that the signal 17 indicates that the generated acoustic alarm is not sufficiently different from other sounds included in the detected audio in respect of one or more of the parameters considered during the further analysis, at step 45 it alters one or more of the parameters which were determined to be insufficiently different. As described above, the determination of which parameter(s) to alter and by how much may be performed by a processing unit of the medical device 10, or alternatively may be performed by the processing unit 14 of the validation device 1. For example, the medical device 10 will change the alarm pattern of the generated acoustic alarm if the result of the further analysis is that the detected audio signal 16 includes one or more other acoustic alarms having a similar pattern to the current generated acoustic alarm. Likewise, the medical device 10 will increase the volume of the generated acoustic alarm if the result of the further analysis is that the detected audio signal 16 includes other sounds (either other alarms or background noise) having a volume similar to or a greater than the volume of the current generated acoustic alarm.

If step 45 is performed after step 41 or step 42 (i.e. the acoustic alarm has not been determined to be included in the detected audio), then which parameters are altered by the medical device will not be based on the results of further analysis by the validation device 1 (since no such further analysis will have been performed). Instead, which parameters to alter will be determined in accordance with pre-defined rules programmed into a memory of either the validation device 1 or the medical device 10. In embodiments in which these predefined rules are programmed into a memory of the validation device 1, the processing unit 14 will determine which parameters should be altered and will generate instructions to the medical device 10 to perform such an alteration. These instructions will be sent to the medical device in the signal 17. In alternative embodiments in which the predefined rules are programmed into a memory of the medical device 10, a processing unit of the medical device will determine which parameters should be altered.

In some embodiments, the predefined rules cause the medical device 10 to increase a volume setting for generated acoustic alarms at step 45. Alternatively or additionally, the predefined rules may cause the medical device 10 to cause the generated acoustic alarm to be emitted by a different loudspeaker at step 45. Some medical devices, for example, may have an integral loudspeaker as well as being connected to a remote loudspeaker (as is usually the case in a silent ICU arrangement). In some embodiments the predefined rules cause the medical device 10 to perform a further action instead of or in addition to altering one or more parameters of the generated acoustic alarm. In some embodiments the further action comprises causing a non-acoustic alarm to be generated. Such a non-acoustic alarm could take the form of a flashing light and/or a message displayed on a screen of the medical device 10. In some embodiments the medical device 10 has the capability to send a message to a paging device of a caregiver, in which case the generation of the non-acoustic alarm may comprise the sending of such a message.

In some embodiments the medical device 10 and/or the validation device 1 stores in a memory a record of which parameters have already been altered and/or which further actions have already been taken in respected of a particular generated acoustic alarm. In such embodiments the pre-defined rules may account for such previous alterations/actions. For example, if the medical device has already increased the volume setting in response to a previous negative validation result, and the subsequent validation result is also negative, the predefined rules may cause the medical device to cause a different loudspeaker to emit the generated acoustic alarm and/or to take a further action.

Once the one or more parameters according to which the acoustic alarm is generated have been altered, at step 46 the medical device 10 generates an acoustic alarm in accordance with the altered parameters and continues to periodically check for signals from the validation device 1.

Preferably the validation method of FIG. 3 is then repeated in respect of the altered acoustic alarm. This may be initiated manually, for example by a member of the medical personnel activating an alarm test function of the medical device 10, 20. In some embodiments, however, an alarm test function will be activated automatically as a result of the acoustic alarm parameters having been changed. In still other embodiments the medical device 10 and/or validation device 1 are configured such that the validation process is automatically triggered every time the medical device 10 generates an acoustic alarm.

If the medical device 10, in response to receiving the signal 17, has caused a different loudspeaker remote from the first loudspeaker (i.e. the different loudspeaker is located such that sound emitted by the different loudspeaker cannot be detected by the microphone 12 of the validation device 1) to emit the generated acoustic alarm, then this alarm cannot be validated by the validation device 1. In some embodiments a further validation device is provided close to the different loudspeaker, in which case preferably the further validation device is then used to validate the emission of the generated acoustic alarm. It will be appreciated that validation of non-acoustic alarms is outside the scope of the present invention.

Application of the invention to a silent ICU arrangement will now be described, with reference to FIG. 5. In a typical silent ICU arrangement, an acoustic alarm generated by a medical device associated with a patient is emitted by a remote alarm unit that is located somewhere outside the room in which the medical device and patient are located (for example the remote alarm unit can be located immediately outside the room in a corridor or another room, or at a nearby staff workstation). When the alarm is emitted by the remote alarm unit, the medical device can be controlled such that it does not itself emit the acoustic alarm or it emits the acoustic alarm at a reduced volume, thereby avoiding or reducing the disturbance to the patient.

Figure 5:
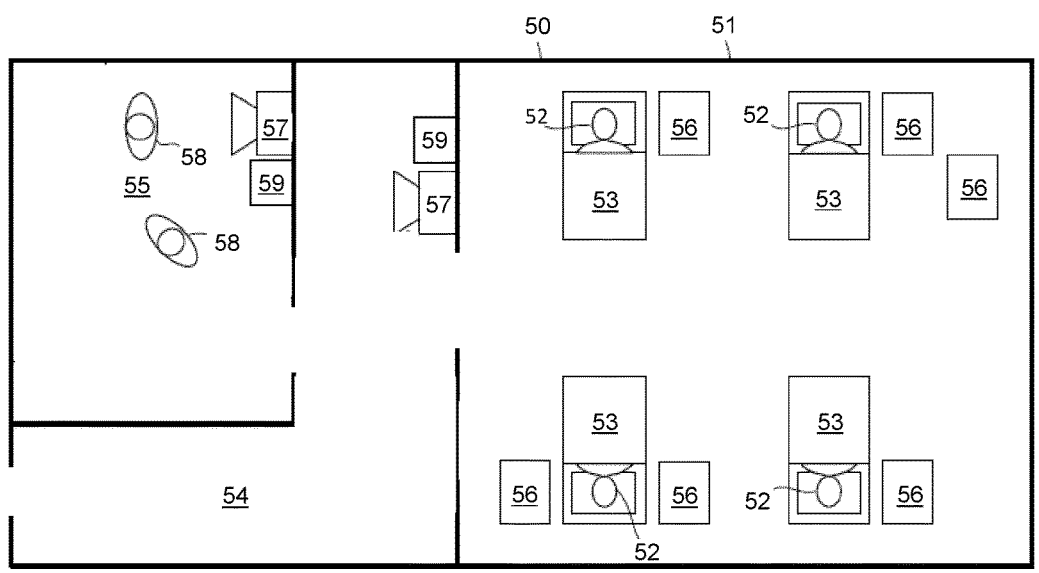
FIG. 5 is an illustration of an alarm detection and validation system in use in a "silent ICU" healthcare environment.

In the example of FIG. 5, a hospital or nursing home environment 50 comprises a patient room 51 in which patients 52 are located in respective beds 53, a corridor 54 outside the patient room 51 and a workstation or room 55 for the healthcare staff 16. Each patient 52 has one or more medical devices 56 associated with them. Each medical device 56 is used at the point of care and can be for monitoring one or more physiological characteristics of the patient 52, such as heart rate, blood pressure, breathing rate, blood oxygen levels, etc, and/or for providing some treatment to the patient 52, such as controlling the administration of an intravenous drug, assisting the patient's breathing, etc.

The medical devices 56 are connected to one or more remote alarm units 57 located somewhere outside the patient room 50 in which the patients 52 and medical devices 56 are located. The medical devices 56 are connected to the remote alarm units 57 using wires or a short or long-range wireless technology, such as Wi-Fi, Bluetooth, ZigBee, or a cellular telecommunications network, etc. Each remote alarm unit 57 comprises a loudspeaker for emitting acoustic alarms generated by the medical devices 56, and a communication interface that enables communications between the remote alarm unit 57 and the medical devices 56. The medical devices 56 also have local loudspeakers, provided either integrally with the main body of the medical device or adjacent to the main body of the medical device.

In some embodiments, the remote alarm units 57 and/or the medical devices 56 further include a means for generating non-acoustic alarms. The means for generating non-acoustic alarms may comprise, for example, a light source that is illuminated or flashed to indicate the alarm condition, and/or a screen on which an alarm message may be displayed. In other or further embodiments, an alarm unit 57 or medical device 56 may alternatively or additionally alert individual members of medical personnel 58 to an alarm condition, for example by sending a message to a pager or mobile communication device (e.g. a mobile telephone) carried by a member of medical personnel 58.

An alarm validation device 59 is provided in proximity to each remote alarm unit 57. In a silent ICU arrangement it is particularly important that the remote alarm unit functions correctly, since the integral loudspeakers of the medical devices are likely to be disabled. The alarm validation devices 59 are therefore configured to validate every alarm sent to the remote alarm units 57 by the medical devices 56. Since it is possible that a failure of the remote alarm units 57 to emit a generated alarm may be caused by a problem with the communications link between the remote alarm units 57 and the medical devices 56, preferably a different communications link is used to connect the validation devices 59 to the medical devices 56. For example, a separate wire may be used between a medical device 56 and a remote alarm unit 57 as between that medical device and a validation device 59. Similarly, where wireless communication technology is employed, preferably a different wireless technology is employed for each communications link.

To ensure that every generated acoustic alarm is validated, each medical device 56 is arranged to send a signal to the validation device 59 associated with the remote alarm unit 57 to which the medical device 56 is using to emit acoustic alarms every time that medical device generates an acoustic alarm. In this manner, a validation process as described above will be carried out in respect of each generated alarm. If the outcome of the validation process is negative (i.e. the validation device 59 does not output a signal to the medical device 56 within the predetermined time period, or the validation device 59 outputs a signal based on it having determined that the audio signal does not include the acoustic alarm generated by the medical device 56) then this indicates that the remote alarm unit 57 has not functioned correctly.

The medical device 56 may then take one or more of the further actions described above. The further action selected by the medical device 56 may be determined, at least in part, on the severity of the medical condition which caused the acoustic alarm to be generated. For example, if the medical condition is of lower urgency, the medical device 56 may as a first step cause a non-acoustic alarm to be generated by the remote alarm unit 57 and/or the medical device itself. If, after performing this action, the alarm has not been dealt within a predetermined period of time, or if the medical condition becomes more urgent, the medical device may take a second further action. The second further action may comprise, for example, emitting the acoustic alarm using the local loudspeaker of the medical device 56. If the medical condition is of high urgency from the outset, then the medical device 56 will in preferred embodiments emit the acoustic alarm using the local loudspeaker as a first further action, and in some embodiments will also cause the remote alarm unit 57 to emit a non-acoustic alarm, and/or send a message directly to a member of medical personnel 58. In this way the risk of an alarm being ignored due to the failure of a remote alarm unit in a silent ICU arrangement can be minimised.

In other embodiments (not illustrated) which do not fall within the scope of the present invention, the alarm detection and validation device may be a completely stand-alone device (i.e. lacking any connection to a medical device). Validation devices according to such embodiments can be used to create a log of acoustic alarms generated by a particular medical device. Such a log can then be used to generate alarm statistics for a particular location, which may then be used to assess and manage the potential for alarm fatigue in that location. Alternatively or additionally, such a log can be used to independently verify that a particular acoustic alarm generated by a medical device was actually emitted in an audible manner. This may be useful, for example, in a legal dispute.

In still other embodiments (not illustrated) which do not fall within the scope of the present invention, the alarm detection and validation device can be used as an interface to link non-compatible medical devices to a centralized alarm management system such as the Philips IntelliSpace Event Management system (i.e. devices which cannot be directly connected, for example because they lack the necessary connectors or run on incompatible operating systems). In such embodiments the alarm validation device is in communication with the centralized alarm management system, but is not in communication with the non-compatible medical devices. The validation device has access to an alarm sound database which contains all alarm sounds that can be issued by the non-compatible medical devices which are to be interfaced. For every alarm sound, the database also contains information which identifies the originating device and the type of alarm. When the validation device detects an acoustic alarm, it analyzes the detected alarm sound using the alarm sound database and thereby identifies the originating device and the type of the alarm. This information is communicated to the centralized alarm management system, which processes it alongside alarm information received from compatible medical devices which are directly connected to the system. In a similar manner, some embodiments (not falling within the scope of the present invention) of the alarm detection and validation device can be used as an interface to pass alarm information between non-compatible medical devices (i.e. medical devices which cannot be directly connected to each other). Thus a patient monitor, for example, can learn that a ventilator has issued an acoustic alarm of a particular type, and can take this into account in its analysis of vital signs data. Alternatively or additionally, the patient monitor can notify a central management system that there is a ventilator alarm, if the patient monitor is connected to such a central management system but the ventilator is not.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An alarm detection and validation device for validating acoustic alarms that have been generated by a medical device, the alarm detection and validation device comprising:
   a microphone arranged to output a first signal corresponding to audio detected by the microphone; and
   a processing unit arranged to:
      receive the first signal from the microphone;
      receive a second signal from the medical device indicating that the medical device has generated an acoustic alarm;
      analyze the first signal to determine whether the detected audio includes the acoustic alarm generated by the medical device by applying a sound classifier to the detected audio so as to identify known alarm sounds included in the detected audio; and
      output a third signal to the medical device based on the result of the analysis of the first signal, if the result of the determination is that the detected audio includes the acoustic alarm generated by the medical device, wherein the third signal comprises an instruction that the medical device alter one or more parameters of the acoustic alarm, wherein the one or more parameters include at least one of alarm volume, alarm pattern, alarm spectral composition, and which loudspeaker is used to emit the alarm.

2. The alarm detection and validation device of claim 1, wherein the processing unit is also arranged to output the third signal if the result of the analysis of the first signal is that the detected audio does not include the acoustic alarm generated by the medical device, and wherein the third signal comprises a notification of the result of the analysis of the first signal.

3. An alarm detection and validation device comprising:
   a memory; and
   a processing unit configured to:
      receive a first signal corresponding to audio detected by a microphone;
      receive a second signal from a medical device indicating that the medical device has generated an acoustic alarm;
      analyze the first signal to determine whether the detected audio includes the acoustic alarm generated by the medical device by applying a sound classifier to the detected audio so as to identify known alarm sounds included in the detected audio;
      determine a current sound pressure level;
      use the determined sound pressure level to compare the volume of an acoustic alarm identified in the detected audio with the volume of other sounds included in the detected audio; and
      output a third signal to the medical device based on the result of the analysis of the first signal, if the result of the analysis of the first signal is that the detected audio includes the acoustic alarm generated by the medical device.

4. The alarm detection and validation device of claim 3, wherein the processing unit is further arranged to:
   determine one or more parameters associated with an acoustic alarm included in the detected audio which has been identified by the processing unit as being generated by the medical device;
   determine one or more parameters associated with a different acoustic alarm included in the detected audio signal which has been identified by the processing unit as being generated by a device other than the medical device; and
   compare the one or more parameters of the acoustic alarm with the one or more parameters of the different acoustic alarm.

5. The alarm detection and validation device of claim 4, wherein the third signal comprises an instruction to the medical device to alter one or more parameters of the acoustic alarm to be different to the one or more parameters of the different acoustic alarm.

6. A medical device comprising:
   a loudspeaker for emitting an acoustic alarm generated by the medical device;
   an alarm detection and validation device according to claim 1, wherein the microphone of the alarm detection and validation device is arranged such that the detected audio includes any acoustic alarms emitted by the loudspeaker; and
   a processing unit arranged to:
      cause the loudspeaker to emit an acoustic alarm;
      send a signal to the alarm detection and validation device indicating that the medical device has generated an acoustic alarm; and
      perform a further action in response to:
         (a) receiving the third signal output by the alarm detection and validation device, wherein the further action is based on the third signal; or
         (b) not receiving a signal from the alarm detection and validation device within a predetermined time period.

7. The medical device of claim 6, wherein the further action comprises one or more of: cause the loudspeaker to continue emitting the acoustic alarm in accordance with the current parameters; alter one or more of the predefined parameters and cause the loudspeaker to emit the acoustic alarm in accordance with the altered parameters; cause the loudspeaker to cease emitting the acoustic alarm; cause a different loudspeaker to emit the acoustic alarm; cause an alternative alarm means to emit a non-acoustic alarm.

8. The medical device of claim 6, wherein the medical device comprises:
   a main body which houses at least the processing unit of the medical device;
   one or more remote components able to be positioned remotely from the main body, which house at least the loudspeaker and the microphone; and
   a communications interface for enabling communication between the processing unit in the main body and the one or more remote components.

9. The medical device of claim 6, wherein the medical device further comprises alternative alarm means for generating a non-acoustic alarm, and wherein the processing unit of the medical device is further arranged to cause the alternative alarm means to generate a non-acoustic alarm:
   (a) if the medical device has not received a signal from the alarm detection and validation device within the predetermined time period; or
   (b) wherein the processing unit of the alarm detection and validation device is also arranged to output the third signal if the result of the analysis of the first signal is that the detected audio does not include the acoustic alarm generated by the medical device, if the third signal is based on the alarm detection and validation device having determined that the detected audio does not include the acoustic alarm generated by the medical device.

10. The medical device of any of claim 6, further comprising an additional loudspeaker located within or adjacent to the main body of the medical device, wherein the processing unit of the medical device is arranged to cause the additional loudspeaker to emit an acoustic alarm:
   (a) if the third signal is based on the alarm detection and validation device having determined that the detected audio does not include the acoustic alarm generated by the medical device; or
   (b) wherein the processing unit of the alarm detection and validation device is also arranged to output the third signal if the result of the analysis of the first signal is that the detected audio does not include the acoustic alarm generated by the medical device, if the third signal is based on the alarm detection and validation device having determined that the detected audio does not include the acoustic alarm generated by the medical device.

11. A method for validating an acoustic alarm generated by a medical device, the method comprising:
   receiving a first signal corresponding to audio detected by a microphone;
   receiving a second signal from a medical device indicating that the medical device has generated an acoustic alarm
   analyzing, with the processing unit, the detected audio to determine whether it includes the acoustic alarm generated by the medical device by applying a sound classifier to the detected audio so as to identify known alarm sounds included in the detected audio; and
   outputting, with the processing unit, a signal to the medical device based on the result of the analysis of the first signal, wherein the third signal comprises an instruction that the medical device alter one or more parameters of the acoustic alarm, wherein the one or more parameters include at least one of alarm volume, alarm pattern, alarm spectral composition, and which loudspeaker is used to emit the alarm.

12. The method of claim 11, further comprising outputting the signal to the medical device if it is determined in that the detected audio does not include the acoustic alarm generated by the medical device.

13. A non-transitory machine-readable medium encoded with instructions for execution by a processor, the non-transitory machine-readable medium comprising:
   instructions for receiving a first signal corresponding to audio detected by a microphone;
   instructions for receiving a second signal from a medical device indicating that the medical device has generated an acoustic alarm
   instructions for analyzing the detected audio to determine whether it includes the acoustic alarm generated by the medical device by applying a sound classifier to the detected audio so as to identify known alarm sounds included in the detected audio; and
   instructions for outputting a signal to the medical device based on the result of the analysis of the first signal, wherein the third signal comprises an instruction that the medical device alter one or more parameters of the acoustic alarm, wherein the one or more parameters include at least one of alarm volume, alarm pattern, alarm spectral composition, and which loudspeaker is used to emit the alarm.

14. The alarm detection and validation device of claim 1, wherein the classifier comprises a classifier that is pre-trained on an alarm sound database to recognize sounds corresponding to acoustic alarms generated by a plurality of different medical devices.

15. The method of claim 11, wherein the classifier comprises a classifier that is pre-trained on an alarm sound database to recognize sounds corresponding to acoustic alarms generated by a plurality of different medical devices.

16. The non-transitory machine-readable storage medium of claim 13, wherein the classifier comprises a classifier that is pre-trained on an alarm sound database to recognize sounds corresponding to acoustic alarms generated by a plurality of different medical devices.

17. The non-transitory machine-readable storage medium of claim 13, further comprising instructions for outputting the third signal if the result of the analysis of the first signal is that the detected audio does not include the acoustic alarm generated by the medical device, and wherein the third signal comprises a notification of the result of the determining.

18. The non-transitory machine-readable storage medium of claim 13, further comprising:
    instructions for determining a current sound pressure level; and
    instructions for using the determined sound pressure level to compare the volume of an acoustic alarm identified in the detected audio with the volume of other sounds included in the detected audio.

19. The non-transitory machine-readable storage medium of claim 18, further comprising:
    instructions for determining one or more parameters associated with an acoustic alarm included in the detected audio which has been identified by the processing unit as being generated by the medical device;
    instructions for determining one or more parameters associated with a different acoustic alarm included in the detected audio signal which has been identified by the processing unit as being generated by a device other than the medical device; and
    instructions for comparing the one or more parameters of the acoustic alarm with the one or more parameters of the different acoustic alarm.

20. The non-transitory machine-readable storage medium of claim 19, wherein the third signal comprises an instruction to the medical device to alter one or more parameters of the acoustic alarm to be different to the one or more parameters of the different acoustic alarm.

* * * * *